US 11,633,224 B2

(12) United States Patent
Hilleli et al.

(10) Patent No.: US 11,633,224 B2
(45) Date of Patent: Apr. 25, 2023

(54) CRYOGEN PUMP

(71) Applicant: ICECURE MEDICAL LTD., Caesarea (IL)

(72) Inventors: Ron Hilleli, Zichron Yaacov (IL); Shai Kaufman, Nir Eliyahu (IL); Naum Muchnik, Yokneam Illit (IL)

(73) Assignee: ICECURE MEDICAL LTD., Caesarea (IL)

( * ) Notice: Subject to any disclaimer, the term of this patent is extended or adjusted under 35 U.S.C. 154(b) by 502 days.

(21) Appl. No.: 16/785,686

(22) Filed: Feb. 10, 2020

(65) Prior Publication Data

US 2021/0244457 A1 Aug. 12, 2021

(51) Int. Cl.
*A61B 18/02* (2006.01)
*A61B 18/00* (2006.01)

(52) U.S. Cl.
CPC .... *A61B 18/02* (2013.01); *A61B 2018/00333* (2013.01); *A61B 2018/00815* (2013.01); *A61B 2018/00821* (2013.01); *A61B 2018/00863* (2013.01)

(58) Field of Classification Search
CPC .......... A61B 18/02; A61B 2018/00333; A61B 2018/00791; A61B 2018/00815; A61B 2018/00821; A61B 2018/00863; A61B 2018/0262; A61B 2018/0293
USPC ...................................... 606/21–26
See application file for complete search history.

(56) References Cited

U.S. PATENT DOCUMENTS

| | | | |
|---|---|---|---|
| 2,319,542 A | 5/1943 | Hall | |
| 2,888,879 A | 6/1959 | Gaarder | |
| 3,234,746 A | 2/1966 | Smith | |
| 3,358,472 A | 12/1967 | Kipling | |
| 3,456,595 A | 7/1969 | Gottzmann et al. | |
| 3,664,344 A | 5/1972 | Bryne | |
| 3,696,813 A | 10/1972 | Wallach | |
| 3,699,775 A | 10/1972 | Cowans | |

(Continued)

FOREIGN PATENT DOCUMENTS

| | | |
|---|---|---|
| CN | 203122580 U | 8/2013 |
| CN | 203641719 U | 6/2014 |

(Continued)

OTHER PUBLICATIONS

EP Application # 21151413.8 Search Report dated Jul. 23, 2021.

(Continued)

*Primary Examiner* — Khadijeh A Vahdat
(74) *Attorney, Agent, or Firm* — Kligler & Associates Patent Attorneys Ltd

(57) ABSTRACT

Apparatus, consisting of a probe, containing a lumen and having a distal end configured to contact tissue of a living subject. A temperature sensor is located at the distal end, and a pump, having a pump motor, is coupled to deliver a cryogenic fluid through the lumen to the distal end of the probe and to receive the cryogenic fluid returning from the probe. There is a separator, coupled to separate the returning cryogenic fluid into a returning cryogenic liquid and a returning cryogenic gas, and a flow meter, coupled to measure a rate of flow of the returning cryogenic gas. A processor is configured to control a rate of pumping of the pump motor in response to a temperature measured by the temperature sensor and the rate of flow of the returning cryogenic gas.

20 Claims, 9 Drawing Sheets

(56) References Cited

U.S. PATENT DOCUMENTS

| | | |
|---|---|---|
| 3,712,306 A | 1/1973 | Bryne |
| 3,736,936 A | 6/1973 | Basilius et al. |
| 3,736,937 A | 6/1973 | Basilius |
| 3,800,552 A | 4/1974 | Sollami |
| 3,845,974 A | 11/1974 | Pelloux-Gervais |
| 3,862,630 A | 1/1975 | Balamuth |
| 3,882,849 A | 5/1975 | Smith |
| 3,938,505 A | 2/1976 | Jamshidi |
| 3,958,443 A | 5/1976 | Berrettini |
| 3,971,383 A | 7/1976 | van Gerven |
| 3,988,029 A | 10/1976 | Gibson |
| 4,082,096 A | 4/1978 | Benson |
| 4,091,634 A | 5/1978 | Shepherd |
| 4,107,946 A | 8/1978 | Potter |
| 4,127,903 A | 12/1978 | Schachar |
| 4,200,104 A | 4/1980 | Harris |
| 4,202,336 A | 5/1980 | van Gerven |
| 4,211,231 A | 7/1980 | Rzasa |
| 4,306,568 A | 2/1981 | Torre |
| 4,279,626 A | 7/1981 | Buchmuller |
| 4,313,306 A | 2/1982 | Torre |
| 4,367,744 A | 1/1983 | Sole |
| 4,376,376 A | 3/1983 | Gregory |
| 4,428,748 A | 1/1984 | Peyman |
| 4,463,458 A | 7/1984 | Seidner |
| 4,481,948 A | 11/1984 | Sole |
| 4,487,253 A | 12/1984 | Malek |
| 4,545,367 A | 10/1985 | Tucci |
| 4,552,208 A | 11/1985 | Sorenson |
| 4,570,626 A | 2/1986 | Norris |
| 4,573,525 A | 3/1986 | Boyd |
| 4,611,654 A | 9/1986 | Buchsel |
| 4,617,018 A | 10/1986 | Nishi |
| 4,676,225 A | 6/1987 | Bartera |
| 4,724,834 A | 2/1988 | Alperovich et al. |
| 4,726,194 A | 2/1988 | Mackay |
| 4,765,396 A | 8/1988 | Seidenberg |
| 4,770,171 A | 9/1988 | Sweren |
| 4,802,475 A | 2/1989 | Weshahy |
| 4,823,790 A | 4/1989 | Alperovich et al. |
| 4,831,856 A | 5/1989 | Gano |
| 4,832,022 A | 5/1989 | Tjulkov et al. |
| 4,946,460 A | 8/1990 | Merry et al. |
| 5,026,387 A | 6/1991 | Thomas |
| 5,047,043 A | 9/1991 | Kubota |
| 5,108,390 A | 4/1992 | Potocky |
| 5,147,355 A | 9/1992 | Friedman |
| 5,188,102 A | 2/1993 | Idemoto |
| 5,214,925 A | 6/1993 | Hoy |
| 5,222,937 A | 6/1993 | Kagawa |
| 5,224,943 A | 7/1993 | Goddard |
| 5,243,826 A | 9/1993 | Longsworth |
| 5,254,082 A | 10/1993 | Takase |
| 5,254,116 A | 10/1993 | Baust |
| 5,261,923 A | 11/1993 | Soares |
| 5,263,957 A | 11/1993 | Davison |
| 5,264,116 A | 11/1993 | Apelian |
| 5,267,960 A | 12/1993 | Hayman et al. |
| 5,275,595 A | 1/1994 | Dobak |
| 5,281,215 A | 1/1994 | Milder |
| 5,295,484 A | 3/1994 | Marcus |
| 5,324,286 A | 6/1994 | Fowle |
| 5,330,745 A | 7/1994 | Mcdow |
| 5,334,181 A | 8/1994 | Rubinsky et al. |
| 5,342,380 A | 8/1994 | Hood |
| 5,361,591 A | 11/1994 | Caldwell |
| 5,363,879 A | 11/1994 | Rhoades |
| 5,391,144 A | 2/1995 | Sakurai |
| 5,411,374 A | 5/1995 | Gram |
| 5,417,073 A | 5/1995 | James |
| 5,423,807 A | 6/1995 | Milder |
| 5,429,138 A | 7/1995 | Jamshidi |
| 5,429,155 A | 7/1995 | Brzyski et al. |
| 5,438,837 A | 8/1995 | Caldwell |
| 5,441,512 A | 8/1995 | Muller |
| 5,445,462 A | 8/1995 | Johnson |
| 5,452,582 A | 9/1995 | Longsworth |
| 5,488,831 A | 2/1996 | Griswold |
| 5,516,505 A | 5/1996 | Mcdow |
| 5,520,682 A | 5/1996 | Baust |
| 5,522,870 A | 6/1996 | Ben-Zion |
| 5,526,821 A | 6/1996 | Jamshidi |
| 5,547,473 A | 8/1996 | Peyman |
| 5,573,532 A | 11/1996 | Chang |
| 5,600,143 A | 2/1997 | Roberts |
| 5,603,221 A | 2/1997 | Maytal |
| 5,616,838 A | 4/1997 | Preston et al. |
| 5,620,479 A | 4/1997 | Diederich |
| 5,683,592 A | 4/1997 | Bartholomew |
| 5,632,743 A | 5/1997 | Clarke |
| 5,647,868 A | 7/1997 | Chinn |
| 5,654,279 A | 8/1997 | Rubinsky |
| 5,658,276 A | 8/1997 | Griswold |
| 5,674,218 A | 10/1997 | Rubinsky et al. |
| 5,687,776 A | 11/1997 | Forgash |
| 5,716,353 A | 2/1998 | Matsuura |
| 5,720,743 A | 2/1998 | Bischof |
| 5,728,130 A | 3/1998 | Ishikawa |
| 5,735,845 A | 4/1998 | Zupkas |
| 5,771,946 A | 6/1998 | Kooy |
| 5,787,940 A | 8/1998 | Bonn |
| 5,800,448 A | 9/1998 | Banko |
| 5,800,487 A | 9/1998 | Mikus |
| 5,814,040 A | 9/1998 | Nelson |
| 5,860,970 A | 1/1999 | Goddard et al. |
| 5,860,971 A | 1/1999 | Clarke |
| 5,868,673 A | 2/1999 | Vesely |
| 5,976,505 A | 2/1999 | Henderson |
| 5,885,276 A | 3/1999 | Ammar |
| 5,899,897 A | 5/1999 | Rabin |
| 5,906,612 A | 5/1999 | Chinn |
| 5,906,628 A | 5/1999 | Miyawaki |
| 5,910,104 A | 6/1999 | Dobak et al. |
| 5,921,982 A | 7/1999 | Lesh |
| 5,935,124 A | 8/1999 | Klumb et al. |
| 5,946,920 A | 9/1999 | Clarke |
| 5,957,918 A | 9/1999 | Griswold |
| 5,976,092 A | 11/1999 | Chinn |
| 5,992,158 A | 11/1999 | Goddard et al. |
| 6,007,571 A | 12/1999 | Neilson et al. |
| 6,012,453 A | 1/2000 | Tsais |
| 6,024,750 A | 2/2000 | Mastri |
| 6,027,499 A | 2/2000 | Johnston et al. |
| 6,032,068 A | 2/2000 | Daniel |
| 6,035,646 A | 3/2000 | Griswold |
| 6,035,657 A | 3/2000 | Dobak |
| 6,036,667 A | 3/2000 | Manna |
| 6,039,730 A | 3/2000 | Rabin |
| 6,041,787 A | 3/2000 | Rubinsky |
| 6,042,342 A | 3/2000 | Orian |
| 6,053,906 A | 4/2000 | Honda |
| 6,063,098 A | 5/2000 | Houser |
| 6,074,412 A | 6/2000 | Mikus et al. |
| 6,032,675 A | 7/2000 | Rubinsky |
| 6,082,400 A | 7/2000 | Tocha |
| 6,059,820 A | 8/2000 | Baronov |
| 6,095,149 A | 8/2000 | Sharkey |
| 6,123,675 A | 9/2000 | Kreizman et al. |
| 6,142,991 A | 11/2000 | Schatzberger |
| 6,145,322 A | 11/2000 | Odashima |
| 6,152,894 A | 11/2000 | Kubler |
| 6,182,666 B1 | 2/2001 | Dobak |
| 6,183,019 B1 | 2/2001 | Owen |
| 6,200,308 B1 | 3/2001 | Pope |
| 6,203,288 B1 | 3/2001 | Kottke |
| 6,206,832 B1 | 3/2001 | Downey |
| 6,212,904 B1 | 4/2001 | Arkharov |
| 6,216,029 B1 | 4/2001 | Paltieli |
| 6,235,018 B1 | 5/2001 | LePivert |
| 6,235,019 B1 | 5/2001 | Lehmann et al. |
| 6,237,355 B1 | 5/2001 | Li |
| 6,251,105 B1 | 6/2001 | Mikus |
| 6,270,494 B1 | 8/2001 | Kovalcheck |
| 6,280,407 B1 | 8/2001 | Manna |

(56) References Cited

U.S. PATENT DOCUMENTS

| | | |
|---|---|---|
| 6,354,088 B1 | 3/2002 | Emmer |
| 6,358,264 B2 | 3/2002 | Banko |
| 6,379,348 B1 | 4/2002 | Onik |
| 6,383,180 B1 | 5/2002 | Lalonde |
| 6,383,181 B1 | 5/2002 | Johnston |
| 6,411,852 B1 | 6/2002 | Danek |
| 6,413,263 B1 | 7/2002 | Lobdill |
| 6,423,009 B1 | 7/2002 | Downey |
| 6,432,102 B2 | 8/2002 | Joye |
| 6,457,212 B1 | 10/2002 | Craig |
| 6,468,268 B1 | 10/2002 | Abboud |
| 6,468,269 B1 | 10/2002 | Korpan |
| 6,471,217 B1 | 10/2002 | Hayfield |
| 6,471,694 B1 | 10/2002 | Kudaravalli et al. |
| 6,482,178 B1 | 11/2002 | Andrews |
| 6,355,033 B1 | 12/2002 | Moorman |
| 6,497,714 B1 | 12/2002 | Ishikawa |
| 6,500,109 B2 | 12/2002 | Tokita |
| 6,500,172 B1 | 12/2002 | Panescu et al. |
| 6,503,246 B1 | 1/2003 | Har-Shai |
| 6,508,814 B2 | 1/2003 | Tortal |
| 6,513,336 B2 | 2/2003 | Zurecki |
| 6,547,784 B1 | 4/2003 | Thompson |
| 6,551,309 B1 | 4/2003 | LePivert |
| 6,562,030 B1 | 5/2003 | Abboud |
| 6,565,556 B1 | 5/2003 | Korpan |
| 6,581,390 B2 | 6/2003 | Emmer |
| 6,582,425 B2 | 6/2003 | Simpson |
| 6,582,426 B2 | 6/2003 | Moorman |
| 6,659,956 B2 | 9/2003 | Barzell |
| 6,631,615 B2 | 10/2003 | Drube |
| 6,640,556 B2 | 11/2003 | Ursan |
| 6,659,730 B2 | 12/2003 | Gram |
| 6,672,095 B1 | 1/2004 | Luo |
| 6,678,621 B2 | 1/2004 | Wiener |
| 6,682,525 B2 | 1/2004 | Lalonde et al. |
| 6,698,423 B1 | 3/2004 | Honkonen |
| 6,702,761 B1 | 3/2004 | Damadian |
| 6,706,037 B2 | 3/2004 | Zvuloni et al. |
| 6,761,715 B2 | 7/2004 | Carroll |
| 6,765,333 B1 | 7/2004 | Mariaucue |
| 6,768,917 B1 | 7/2004 | Van Vaals |
| 6,772,766 B2 | 8/2004 | Gallo |
| 6,786,902 B1 | 9/2004 | Rabin |
| 6,789,545 B2 | 9/2004 | Littrup et al. |
| 6,824,543 B2 | 11/2004 | Lentz |
| 6,852,110 B2 | 2/2005 | Roy et al. |
| 6,852,706 B1 | 2/2005 | Heber-Katz |
| 6,858,025 B2 | 2/2005 | Maurice |
| 6,866,624 B2 | 3/2005 | Chornenky et al. |
| 6,869,439 B2 | 3/2005 | White |
| 6,889,695 B2 | 5/2005 | Pankratov |
| 6,898,940 B2 | 5/2005 | Gram |
| 6,908,472 B2 | 6/2005 | Wiener |
| 6,910,510 B2 | 6/2005 | Gale |
| 6,913,604 B2 | 7/2005 | Mihalik |
| 6,918,869 B2 | 7/2005 | Shaw et al. |
| 6,929,639 B2 | 8/2005 | Lafontaine |
| 6,932,771 B2 | 8/2005 | Whitmore |
| 6,936,045 B2 | 8/2005 | Yu |
| 6,939,346 B2 | 9/2005 | Kannenberg et al. |
| 6,942,659 B2 | 9/2005 | Lehmann |
| 6,945,477 B2 | 9/2005 | Lambert et al. |
| 6,951,569 B2 | 10/2005 | Nohilly |
| 6,954,977 B2 | 10/2005 | Maguire |
| 6,995,493 B2 | 2/2006 | Isoda |
| 7,001,378 B2 | 2/2006 | Von |
| 7,025,762 B2 | 4/2006 | Johnston |
| 7,025,767 B2 | 4/2006 | Schaefer |
| 7,101,367 B2 | 5/2006 | Xiao |
| 7,071,690 B2 | 7/2006 | Butts |
| 7,081,111 B2 | 7/2006 | Svaasand |
| 7,083,612 B2 | 8/2006 | Littrup et al. |
| 7,128,347 B2 | 10/2006 | Kerin |
| 7,128,738 B2 | 10/2006 | Littrup et al. |
| 7,128,739 B2 | 10/2006 | Prakash |
| 7,137,978 B2 | 11/2006 | Levin |
| 7,144,228 B2 | 12/2006 | Emmer |
| 7,151,374 B2 | 12/2006 | Doty |
| 7,156,840 B2 | 1/2007 | Lentz et al. |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,192,426 B2 | 3/2007 | Baust et al. |
| 7,250,046 B1 | 3/2007 | Fallat |
| 7,207,985 B2 | 4/2007 | Duong |
| 7,213,400 B2 | 5/2007 | Dickerson |
| 7,223,080 B2 | 5/2007 | Duron |
| 7,252,648 B2 | 8/2007 | Honda |
| 7,255,693 B1 | 8/2007 | Johnston |
| 7,273,479 B2 | 9/2007 | Up et al. |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Von |
| 7,318,327 B2 | 1/2008 | Dickerson |
| 7,344,530 B2 | 3/2008 | Bischof |
| 7,344,531 B2 | 3/2008 | Bischof |
| 7,354,434 B2 | 4/2008 | Zvuloni |
| 7,357,797 B2 | 4/2008 | Ryba |
| 7,361,187 B2 | 4/2008 | Duong |
| 7,381,207 B2 | 6/2008 | Duong |
| 7,407,501 B2 | 8/2008 | Zvuloni |
| 7,422,583 B2 | 9/2008 | Maurice |
| 7,425,211 B2 | 9/2008 | Levin et al. |
| 7,458,379 B2 | 12/2008 | Littrup et al. |
| 7,458,968 B2 | 12/2008 | Carroll |
| 7,469,718 B2 | 12/2008 | Lambert et al. |
| 7,481,806 B2 | 1/2009 | Levin |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 7,731,711 B2 | 6/2010 | Levin |
| 7,780,657 B2 | 8/2010 | Abboud et al. |
| 7,803,154 B2 | 9/2010 | Toubia et al. |
| 7,921,657 B2 | 4/2011 | Littrup et al. |
| 7,938,822 B2 | 5/2011 | Berzak et al. |
| 7,967,814 B2 | 6/2011 | Levin |
| 7,967,815 B1 | 6/2011 | Berzak et al. |
| 3,080,005 A1 | 12/2011 | Berzak et al. |
| 8,092,448 B2 | 1/2012 | DeLonzor |
| 3,162,812 A1 | 4/2012 | Shai et al. |
| 8,187,264 B2 | 5/2012 | Kobayashi |
| 8,348,855 B2 | 1/2013 | Hillely et al. |
| 8,418,480 B2 | 4/2013 | Danley et al. |
| 8,475,448 B2 | 7/2013 | Sharareh et al. |
| 8,517,749 B2 | 8/2013 | Marshall |
| 8,551,081 B2 | 10/2013 | Baust et al. |
| 3,591,505 A1 | 11/2013 | Sharon et al. |
| 8,579,892 B2 | 11/2013 | Hoey et al. |
| 8,671,700 B2 | 3/2014 | Duong et al. |
| 8,685,014 B2 | 4/2014 | Babkin et al. |
| 8,709,005 B2 | 4/2014 | Berzak et al. |
| 8,784,409 B2 | 7/2014 | Robilotto et al. |
| 8,814,850 B2 | 8/2014 | Babkin et al. |
| 8,845,628 B2 | 9/2014 | Babkin et al. |
| 8,906,004 B2 | 12/2014 | Berzak et al. |
| 8,998,888 B2 | 4/2015 | Baust et al. |
| 9,039,689 B2 | 5/2015 | Berzak et al. |
| 9,050,075 B2 | 6/2015 | Berzak et al. |
| 9,101,343 B2 | 8/2015 | Duong et al. |
| 9,125,689 B2 | 9/2015 | Mielekamp |
| 9,144,461 B2 | 9/2015 | Kruecker et al. |
| 9,237,919 B2 | 1/2016 | Maschke |
| 9,316,215 B2 | 4/2016 | Mackey |
| 9,408,654 B2 | 8/2016 | Baust et al. |
| 9,441,997 B2 | 9/2016 | Downie et al. |
| 9,808,302 B2 | 11/2017 | Berzak et al. |
| 9,956,024 B2 | 5/2018 | Mahrouche et al. |
| 10,022,175 B2 | 7/2018 | Abboud et al. |
| 10,054,262 B2 | 8/2018 | Baust et al. |
| 10,098,685 B2 | 10/2018 | Lalonde et al. |

(56) References Cited

U.S. PATENT DOCUMENTS

| | | | |
|---|---|---|---|
| 10,159,522 | B2 | 12/2018 | Littrup et al. |
| 10,213,244 | B2 | 2/2019 | Fourkas et al. |
| 10,363,081 | B2 | 7/2019 | Clarke |
| 10,383,686 | B2 | 8/2019 | Panescu et al. |
| 10,485,602 | B2 | 11/2019 | Geiselhart |
| 10,531,656 | B2 | 1/2020 | Schryver |
| 10,702,251 | B2 | 7/2020 | Nevo |
| 10,828,080 | B2 | 11/2020 | George et al. |
| 10,859,211 | B2 | 12/2020 | Bollinger |
| 11,026,737 | B2 | 6/2021 | Baust et al. |
| 11,060,778 | B2 | 7/2021 | Jankowsky et al. |
| 11,266,458 | B2 | 3/2022 | Perron et al. |
| 2001/0047129 | A1 | 11/2001 | Hall |
| 2002/0016540 | A1 | 2/2002 | Mikus |
| 2002/0022832 | A1 | 2/2002 | Mikus |
| 2002/0040220 | A1 | 4/2002 | Zvuloni et al. |
| 2002/0042609 | A1 | 4/2002 | Kelman et al. |
| 2002/0077654 | A1 | 6/2002 | Javier |
| 2002/0085921 | A1 | 7/2002 | Gram |
| 2002/0144509 | A1 | 10/2002 | Chalk |
| 2002/0156469 | A1 | 10/2002 | Von |
| 2002/0157402 | A1 | 10/2002 | Drube |
| 2002/0160640 | A1 | 10/2002 | Korpan |
| 2002/0161385 | A1 | 10/2002 | Wiener |
| 2003/0060762 | A1 | 3/2003 | Zvuloni |
| 2003/0079480 | A1 | 5/2003 | Emmer |
| 2003/0126867 | A1 | 7/2003 | Drube |
| 2003/0135119 | A1 | 7/2003 | Lee |
| 2003/0181897 | A1 | 9/2003 | Thomas |
| 2003/0220635 | A1 | 11/2003 | Knowlton et al. |
| 2004/0024391 | A1 | 2/2004 | Cytron |
| 2004/0024392 | A1 | 2/2004 | Lewis et al. |
| 2004/0055316 | A1 | 3/2004 | Emmer |
| 2004/0078033 | A1 | 4/2004 | Levin et al. |
| 2004/0106841 | A1 | 6/2004 | Shaw et al. |
| 2004/0210212 | A1 | 10/2004 | Maurice |
| 2004/0215178 | A1 | 10/2004 | Maurice |
| 2005/0016185 | A1 | 1/2005 | Emmer |
| 2005/0038422 | A1 | 2/2005 | Maurice |
| 2005/0043725 | A1 | 2/2005 | Duong et al. |
| 2005/0056027 | A1 | 3/2005 | White |
| 2005/0086949 | A1 | 4/2005 | Noble |
| 2005/0106153 | A1 | 5/2005 | Nordouist |
| 2005/0159735 | A1 | 7/2005 | Walton et al. |
| 2005/0177147 | A1 | 8/2005 | Vancelette |
| 2005/0192564 | A1 | 9/2005 | Cosman |
| 2005/0198972 | A1 | 9/2005 | Lentz et al. |
| 2005/0214268 | A1 | 9/2005 | Cavanagh |
| 2005/0261671 | A1* | 11/2005 | Baust .............. A61B 18/02 606/22 |
| 2005/0274127 | A1 | 12/2005 | Drube et al. |
| 2005/0274142 | A1 | 12/2005 | Corey |
| 2005/0288658 | A1 | 12/2005 | Littrup et al. |
| 2006/0049274 | A1 | 3/2006 | Hume |
| 2006/0053165 | A1 | 3/2006 | Hume |
| 2006/0079867 | A1 | 4/2006 | Berzak et al. |
| 2006/0122590 | A1 | 6/2006 | Bliweis |
| 2006/0155267 | A1 | 7/2006 | Berzak |
| 2006/0155268 | A1 | 7/2006 | Amir |
| 2006/0253114 | A1 | 11/2006 | Saadat |
| 2006/0264920 | A1 | 11/2006 | Duong |
| 2006/0293647 | A1 | 12/2006 | McRae |
| 2007/0000259 | A1 | 1/2007 | Brook |
| 2007/0043342 | A1 | 2/2007 | Kleinberger |
| 2007/0088217 | A1 | 4/2007 | Babaev |
| 2007/0093710 | A1 | 4/2007 | Maschke |
| 2007/0123815 | A1 | 5/2007 | Mark |
| 2007/0129626 | A1 | 6/2007 | Mahesh et al. |
| 2007/0129629 | A1 | 6/2007 | Beauregard |
| 2007/0149959 | A1 | 6/2007 | DeLonzor |
| 2007/0153969 | A1 | 7/2007 | Maschke |
| 2007/0166171 | A1 | 7/2007 | Kondo |
| 2007/0167939 | A1 | 7/2007 | Duong |
| 2007/0244474 | A1 | 10/2007 | DeLonzor et al. |
| 2007/0276360 | A1 | 11/2007 | Johnston |
| 2007/0277550 | A1 | 12/2007 | Li et al. |
| 2008/0027419 | A1 | 1/2008 | Hamel |
| 2008/0039745 | A1 | 2/2008 | Babaev |
| 2008/0051774 | A1 | 2/2008 | Ofir |
| 2008/0051776 | A1 | 2/2008 | Bliweis |
| 2008/0097251 | A1 | 4/2008 | Babaev |
| 2008/0114346 | A1 | 5/2008 | Levin et al. |
| 2008/0115509 | A1 | 5/2008 | Gullickson |
| 2008/0119834 | A1 | 5/2008 | Vancelette |
| 2008/0119838 | A1 | 5/2008 | Vancelette |
| 2008/0125764 | A1 | 5/2008 | Vancelette et al. |
| 2008/0140061 | A1 | 6/2008 | Toubia et al. |
| 2008/0319433 | A1 | 12/2008 | Geiselhart |
| 2009/0011032 | A1 | 1/2009 | LePivert |
| 2009/0149957 | A1 | 6/2009 | Ross et al. |
| 2009/0163902 | A1 | 6/2009 | DeLonzor et al. |
| 2009/0182320 | A1 | 7/2009 | DeLonzor et al. |
| 2009/0192505 | A1* | 7/2009 | Askew .............. A61M 16/0463 424/9.4 |
| 2010/0057063 | A1 | 3/2010 | Arless et al. |
| 2010/0256621 | A1 | 10/2010 | Babkin et al. |
| 2011/0082351 | A1 | 4/2011 | Razzaque et al. |
| 2011/0306958 | A1* | 12/2011 | Berzak ................. A61B 18/02 606/24 |
| 2012/0316558 | A1 | 12/2012 | Hendriks et al. |
| 2014/0169993 | A1 | 6/2014 | Berzak et al. |
| 2014/0194863 | A1* | 7/2014 | Berzak .............. A61B 18/0218 606/25 |
| 2014/0350537 | A1 | 11/2014 | Baust et al. |
| 2015/0126987 | A1 | 5/2015 | Semenov et al. |
| 2015/0300344 | A1 | 10/2015 | Berzak et al. |
| 2016/0135864 | A1 | 5/2016 | Babkin et al. |
| 2016/0249970 | A1 | 9/2016 | Yu et al. |
| 2019/0175395 | A1 | 6/2019 | Kim |
| 2019/0254731 | A9 | 8/2019 | Sperling et al. |
| 2019/0290348 | A1 | 9/2019 | Clarke |
| 2019/0328437 | A1 | 10/2019 | Perron et al. |
| 2019/0390822 | A1 | 12/2019 | Brothers |
| 2020/0015750 | A1 | 1/2020 | Pike et al. |
| 2020/0121498 | A1 | 4/2020 | Baust et al. |
| 2020/0297403 | A1 | 9/2020 | Kochavi |
| 2020/0378556 | A1 | 12/2020 | Wowk et al. |
| 2021/0177482 | A1 | 6/2021 | Tegg et al. |
| 2021/0239257 | A1 | 8/2021 | Stautner |
| 2022/0287757 | A1 | 9/2022 | Gong et al. |
| 2022/0304737 | A1 | 9/2022 | Pang et al. |

FOREIGN PATENT DOCUMENTS

| | | |
|---|---|---|
| CN | 203873871 U | 10/2014 |
| CN | 204219026 U | 3/2015 |
| CN | 204797984 U | 11/2015 |
| CN | 103784193 B | 12/2015 |
| CN | 207870952 U | 9/2018 |
| CN | 208511163 U | 2/2019 |
| CN | 208541399 U | 2/2019 |
| CN | 109431595 B | 3/2019 |
| CN | 109674525 A | 4/2019 |
| CN | 208677560 U | 4/2019 |
| CN | 208693430 U | 4/2019 |
| CN | 208693431 U | 4/2019 |
| CN | 209032618 U | 6/2019 |
| CN | 109984734 A | 7/2019 |
| CN | 209059412 U | 7/2019 |
| CN | 209153957 U | 7/2019 |
| CN | 209301311 U | 8/2019 |
| CN | 209326130 U | 8/2019 |
| CN | 110236671 A | 9/2019 |
| CN | 209360883 U | 9/2019 |
| CN | 209470383 U | 10/2019 |
| CN | 209574862 U | 11/2019 |
| CN | 209751207 U | 12/2019 |
| CN | 209826947 U | 12/2019 |
| CN | 209826949 U | 12/2019 |
| CN | 209842088 U | 12/2019 |
| CN | 209847361 U | 12/2019 |
| CN | 110251224 B | 2/2020 |
| CN | 210019627 U | 2/2020 |
| CN | 210019628 U | 2/2020 |

(56) References Cited

FOREIGN PATENT DOCUMENTS

| | | | |
|---|---|---|---|
| CN | 210056206 U | 2/2020 |
| CN | 211094644 U | 7/2020 |
| CN | 213216941 U | 5/2021 |
| CN | 214010591 U | 8/2021 |
| DE | 202004008875 U1 | 8/2004 |
| EP | 3292922 B1 | 11/1988 |
| EP | 395307 A2 | 10/1990 |
| EP | 570301 A1 | 11/1994 |
| EP | 0550666 B1 | 1/1999 |
| EP | 919197 B1 | 2/2005 |
| EP | 2593028 B1 | 8/2017 |
| GB | 1108905 A | 4/1968 |
| GB | 1473856 A | 5/1977 |
| GB | 1534472 A | 12/1978 |
| GB | 2321531 A | 7/1998 |
| GB | 2336781 A | 11/1999 |
| GB | 2337000 A | 11/1999 |
| GB | 2409815 A1 | 7/2005 |
| JP | 2004041428 A1 | 2/2004 |
| JP | 2004275732 A | 10/2004 |
| JP | 2007167100 A | 7/2007 |
| WO | 3303961 A1 | 11/1983 |
| WO | 9637158 A1 | 11/1996 |
| WO | 9639960 A1 | 12/1996 |
| WO | 9947876 A1 | 9/1999 |
| WO | 200137919 A2 | 5/2001 |
| WO | 200141683 A3 | 6/2001 |
| WO | 200197702 A1 | 12/2001 |
| WO | 3202026 A1 | 1/2002 |
| WO | 0211638 A1 | 2/2002 |
| WO | 33015651 A1 | 2/2003 |
| WO | 2004051409 A2 | 6/2004 |
| WO | 2004060465 A2 | 7/2004 |
| WO | 2004089183 A1 | 10/2004 |
| WO | 2004093635 A2 | 11/2004 |
| WO | 2005000106 A2 | 1/2005 |
| WO | 2005098308 A1 | 10/2005 |
| WO | 2006116457 A2 | 11/2006 |
| WO | 2006127467 A2 | 11/2006 |
| WO | 2007028232 A1 | 3/2007 |
| WO | 2007076123 A2 | 7/2007 |
| WO | 2007086056 A2 | 8/2007 |
| WO | 2007129308 A2 | 11/2007 |
| WO | 2013067421 A2 | 5/2013 |
| WO | 2014068262 A1 | 5/2014 |
| WO | 2014137383 A1 | 9/2014 |
| WO | 2018184938 A1 | 10/2018 |
| WO | 2021027682 A1 | 2/2021 |
| WO | 2021258840 A1 | 12/2021 |

OTHER PUBLICATIONS

Castillo-Dominguez et al., "Cryostat and CCD for MEGARA at GTC," Conference Paper in Proceedings of SPIE—The International Society for Optical Engineering, pp. 2-11, Sep. 2012.

Douglas, Jr., et al., "Cryosurgial Denervation of the Heart: Acute and Chronic Effects," The Journal of Thoracic and Cardiovascular Surgery, vol. 100, pp. 198-209, year 1990.

JP Application # 202112530 Office Action dated Aug. 23, 2022.

EP Application #22174876.7 Search Report dated Nov. 4, 2022.

Zhang et al., "Two phase flow characteristics of liquid nitrogen in vertically upward 0.5 and 1.0 mm micro-tubes Visualization studies", Cryogenics, vol. 49, issue 10, pp. 565-575, Oct. 2009.

Qi et al., "Development and performance test of a cryoprobe with heat transfer enhancement configuration", Cryogenics, vol. 46, pp. 881-887, year 2006.

Qi et al., "Flow boiling of liquid nitrogen in micro-tubes: Part I—onset of nucleate boiling, two phase flow instability and two phase flow pressure drop", International Journal of Heat and Mass Transfer, vol. 50, pp. 4999-5016, year 2007.

Qi et al., "Flow boiling of liquid nitrogen in micro-tubes: Part II—heat transfer characteristics and critical heat flux", International Journal of Heat and Mass Transfer, vol. 50, pp. 5017-5030, year 2007.

\* cited by examiner

CRYOGEN PUMP

FIELD OF THE INVENTION

This invention relates generally to pumps, and specifically to pumping cryogenic materials.

BACKGROUND OF THE INVENTION

Pumps for cryogenic materials have to be able to overcome limitations caused by the extreme cold, such as reduced elasticity, so as to operate effectively. Systems and methods for improving the efficiency of cryogenic pumps are known in the art.

U.S. Pat. No. 2,888,879 to Gaarder describes pumping of cryogenically cooled liquified gases and in particular pumping liquid oxygen. The pump is of the immersion type where the pump resides within the cryogen container and is therefor cooled by the cryogen itself.

U.S. Pat. No. 3,456,595 to Gottzmann et al describes a pump which serves two purposes. The first is to pump cryogens and the second is to meter the volume of flow by means of counting piston cycles through which a cryogen flows.

U.S. Pat. No. 3,958,443 to Berrettini describes apparatus for proving and calibrating meters used to measure the amount of cryogen dispensed from a storage receptacle.

U.S. Pat. No. 5,616,838 to Preston et al. describes a cryogenic meter that is mounted in an insulated container having an inlet and outlet in circuit with a liquid natural gas delivery flow path.

U.S. Pat. No. 6,203,288 to Kottke describes a reciprocating pump that includes a cylinder with a closed interior compartment. The pump may be used for pumping a cryogen.

U.S. Pat. No. 6,659,730 to Gram et al. describes apparatus for supplying both cryogenic liquid and vapor from a storage tank to a pump to reduce the need for venting. The pump is operable to pump cryogenic liquid or a mixture of liquid and vapor.

U.S. Pat. Nos. 1,192,426 and 8,551,081 to Baust et al. describe a cryosurgical system for supplying cryogen to a probe. The system includes a container filled with cryogen that has a bellows of a pump submerged within the cryogen.

U.S. Pat. No. 8,418,480 to Danley et al. describes a cooling system that employs a single-acting positive displacement bellows pump to transfer a cryogenic liquid such as liquid nitrogen from a storage Dewar to a heat exchanger coupled to a measurement chamber of an instrument, U.S. Pat. No. 8,671,700 to Duong et al. describes a cryogenic fluid generator that includes at least one pump assembly having an actuator mounted to a container assembly.

U.S. Pat. Nos. 8,998,888 and 9,408,654 to Baust et al. describe a cryogenic medical device for delivery of subcooled liquid cryogen to various configurations of cryoprobes. The cryoprobes may be used for the treatment of damaged, diseased, cancerous or other unwanted tissues.

U.S. Pat. No. 9,441,997 to Downie et al. describes a method of measuring the physical properties of a two-phase fluid using at least one piezoelectric oscillator immersed in the two-phase fluid.

U.S. Patent Application 2005/0274127 to Drube et al. describes a mobile system for dispensing cryogenic liquid to a use point. The system includes a low pressure bulk tank containing a supply of cryogenic liquid and a high pressure sump in communication with the bulk tank so as to receive cryogenic liquid from the tank.

U.S. Patent Application 2010/0256621 to Babkin et al. describes cryoablation systems that drive liquid cryogen or refrigerant along a closed fluid pathway without evaporation of the liquid cryogen.

U.S. Patent Applications 2014/0169993 and 2015/0300344 to Berzak et al. describe a cryogen pump that includes a pump section having a bellows with an inlet opening at a first end and an exit opening.

SUMMARY OF THE INVENTION

An embodiment of the present invention provides apparatus, consisting of:

a probe, containing a lumen and having a distal end configured to contact tissue of a living subject;

a temperature sensor located at the distal end;

a pump, having a pump motor, coupled to deliver a cryogenic fluid through the lumen to the distal end of the probe and to receive the cryogenic fluid returning from the probe;

a separator, coupled to separate the returning cryogenic fluid into a returning cryogenic liquid and a returning cryogenic gas;

a flow meter, coupled to measure a rate of flow of the returning cryogenic gas; and a processor configured to control a rate of pumping of the pump motor in response to a temperature measured by the temperature sensor and the rate of flow of the returning cryogenic gas.

In a disclosed embodiment the pump is a piston pump.

In another disclosed embodiment the pump is a bellows pump.

In yet another disclosed embodiment, while the temperature reduces, the processor sets the rate of pumping to a preset high rate irrespective of the rate of flow of the returning cryogenic gas.

Typically, when the temperature has reduced to a predetermined steady-state value, the processor sets the rate of pumping to a preset high rate until the rate of flow of the returning cryogenic gas reduces from a measured peak high value rate of flow to a predetermined lower rate of flow.

In an alternative embodiment, when the rate of flow of the returning cryogenic gas includes the predetermined lower rate of flow, the processor reduces the rate of pumping to a preset rate lower than the preset high rate. Typically, when the rate of pumping has been reduced to the lower preset rate, the processor increases the rate of pumping when at least one of the temperature and the rate of flow changes.

In a further alternative embodiment the predetermined lower rate of flow is a preset percentage, less than 100%, of the measured peak high value rate of flow. The preset percentage may be 50%.

In a yet further alternative embodiment, when the temperature is a first steady-state temperature measured by the temperature sensor the processor sets the rate of pumping at a first rate, and when the temperature is a second steady-state temperature less than the first steady-state temperature, the processor sets the rate of pumping at a second rate greater than the first rate.

There is further provided, according to an embodiment of the present invention, a method, consisting of:

providing a probe containing a lumen and having a distal end, that is configured to contact tissue of a living subject;

locating a temperature sensor at the distal end;

coupling a pump, comprising a pump motor, to deliver a cryogenic fluid through the lumen to the distal end of the probe and to receive the cryogenic fluid returning from the probe;

separating the returning cryogenic fluid into a returning cryogenic liquid and a returning cryogenic gas;

measuring a rate of flow of the returning cryogenic gas; and controlling a rate of pumping of the pump motor in response to a temperature measured by the temperature sensor and the rate of flow of the returning cryogenic gas.

The present disclosure will be more fully understood from the following detailed description of the embodiments thereof, taken together with the drawings, in which:

DETAILED DESCRIPTION OF EMBODIMENTS

Overview

Figure 1:
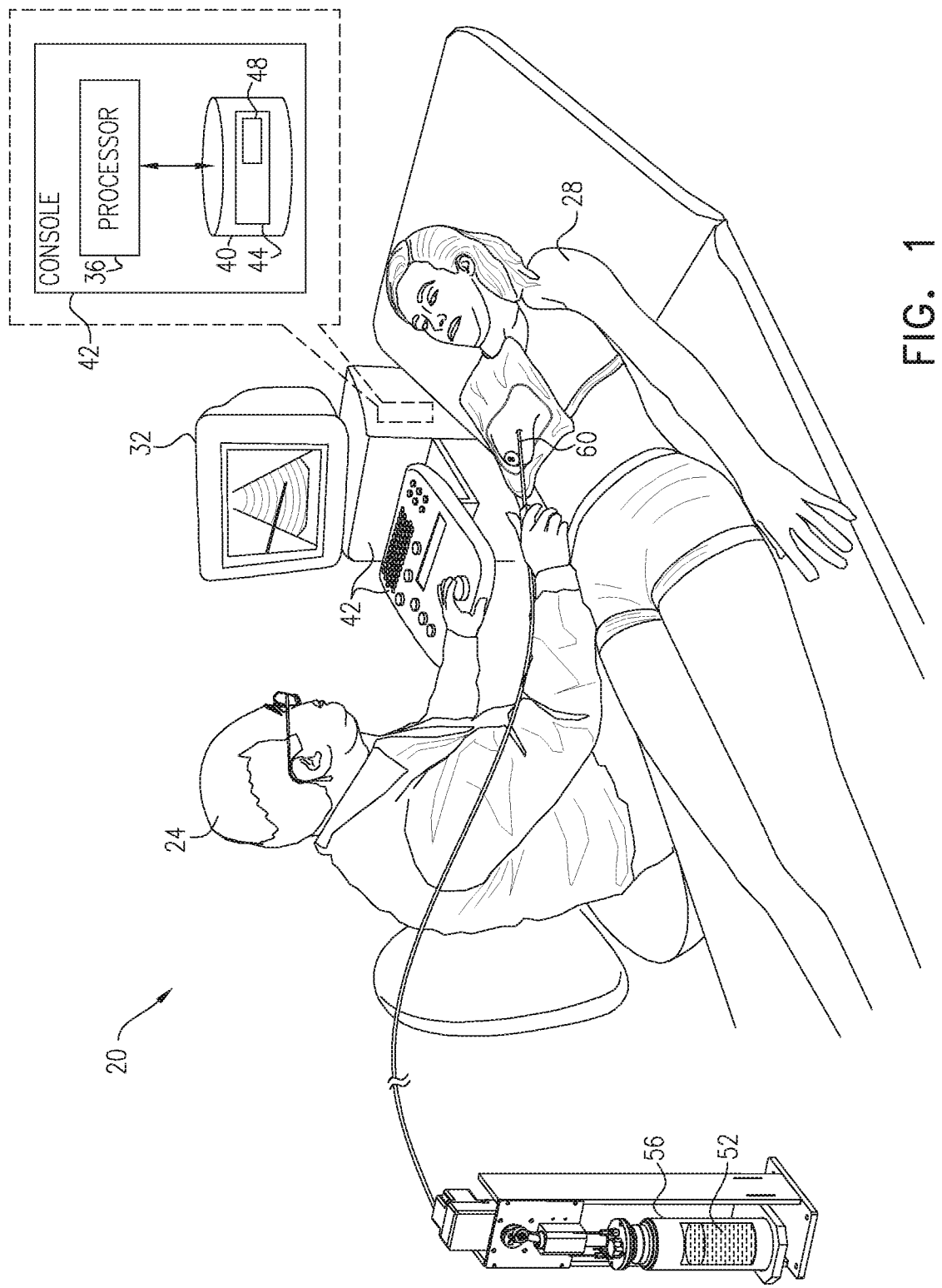
FIG. 1 is a schematic illustration of an apparatus being used for a procedure, according to an embodiment of the present invention.

In contrast to prior art cryogenic pump systems, embodiments of the present invention measure a temperature achieved by cryogenic fluid delivery to a probe as well as a flow rate of returning cryogenic gas from the probe. Using the two measurements enables embodiments of the invention to reduce the volume of cryogenic liquid required to cool the probe to a low temperature steady state. The reduction in volume occurs both during a transition to the low temperature steady state, as well as in the steady state itself.

Thus, in embodiments of the present invention apparatus comprises a probe containing a lumen and a distal end configured to contact tissue of a living subject. A temperature sensor is located at the distal end, and the apparatus comprises a pump, having a pump motor, that is coupled to deliver a cryogenic fluid through the lumen to the distal end of the probe and to receive the cryogenic fluid returning from the probe.

The apparatus further comprises a separator, coupled to separate the returning cryogenic fluid into a returning cryogenic liquid and a returning cryogenic gas, and a flow meter, that is coupled to measure a rate of flow of the returning cryogenic gas. A processor is configured to control a rate of pumping of the pump motor in response to a temperature measured by the temperature sensor and the rate of flow of the returning cryogenic gas.

DETAILED DESCRIPTION

In the following description, like elements in the drawings are identified by like numerals.

Reference is now made to FIG. 1, which is a schematic illustration of an apparatus 20 being used for a procedure, according to an embodiment of the present invention. By way of example the procedure assumed in the following description is on a breast tumor, but it will be understood that apparatus 20 may be used for other procedures, such as on a prostate or kidney tumor, and all such procedures are considered to be comprised within the scope of the present invention.

The procedure is performed by a physician 24 on a patient 28, and the physician is able to observe results of the procedure on a display 32 comprised in apparatus 20. (Typically the procedure on the breast tumor includes performing an ultrasound scan of the breast of patient 28, and presenting results of the scan on display 32. The scan is normally performed by an ultrasound professional, other than physician 24. Details of the ultrasound scan are not relevant to the present disclosure, and for simplicity the ultrasound professional is not shown in FIG. 1.)

Apparatus 20 is controlled by a processor 36, which is coupled to a memory 40 wherein is stored software 44 for operation of the apparatus. Processor 36 and memory 40 are installed in an operating console 42. Software 44 in memory 40 may be downloaded to the processor in electronic form, over a network, for example. Alternatively or additionally, the software may be provided on non-transitory tangible media, such as optical, magnetic, or electronic storage media. Software 44 includes software for an apparatus operation algorithm 48, comprising steps executed by the processor in operating apparatus 20. Apparatus operation algorithm 48 is described in more detail below.

In the procedure on the breast tumor, apparatus 20 is used to insert a cryogenic fluid 52, initially held in a pump 56, into a probe 60 which has a distal end that is inserted into proximity with the tumor. Fluid 52 is initially in the form of a liquid, but during the procedure the fluid may change from a liquid to a liquid/gas mixture, or even to a completely gaseous state. Except where otherwise stated, cryogenic fluid 52 is herein assumed, by way of example, to comprise liquid or gaseous nitrogen. However, it will be understood that other cryogenic fluids, such as cryogenic argon, may be used in apparatus 20, and all such cryogenic fluids are assumed to be comprised within the scope of the present invention. Pump 56 is connected to probe 60, which physician 24 manipulates so as to correctly position the probe distal end with respect to the tumor. (The manipulation is typically assisted by the physician observing the ultrasound scan referred to above.) Pump 56 and probe 60 are both described in more detail below.

Figure 2:
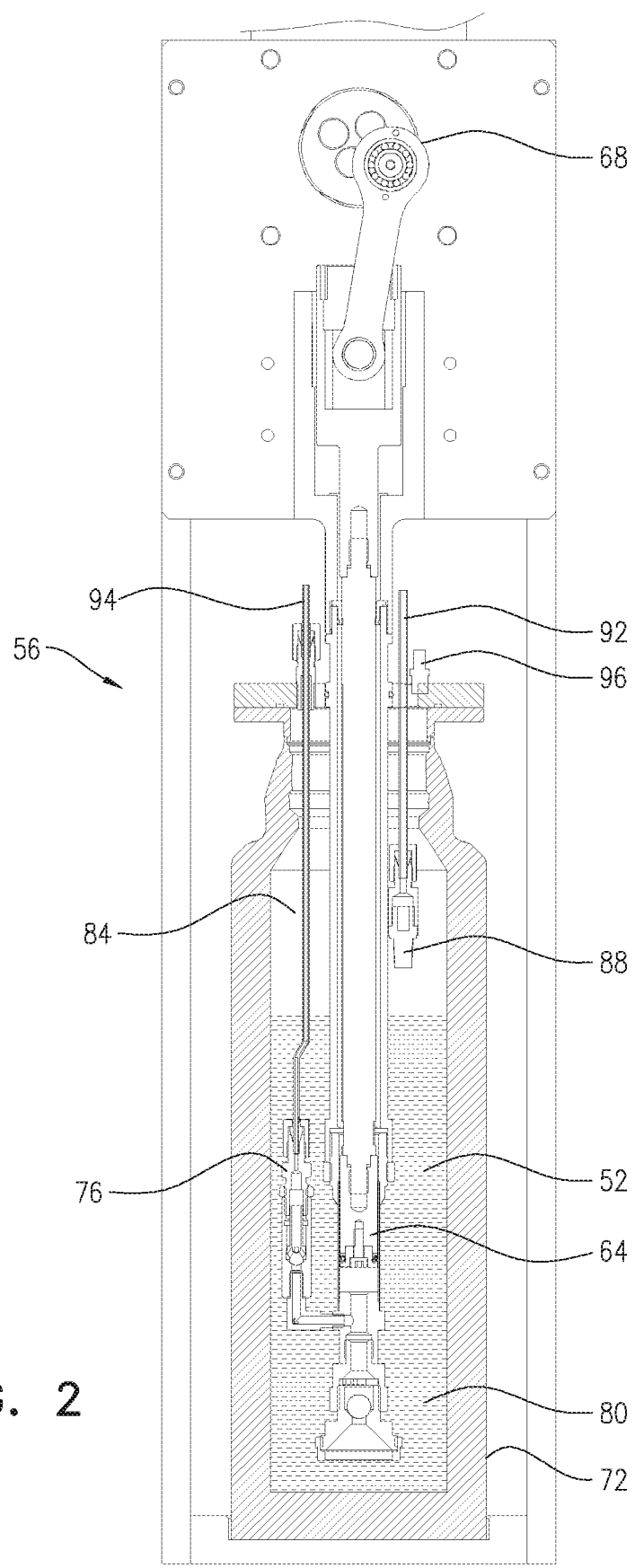
FIG. 2 is a schematic diagram of a pump, according to an embodiment of the present invention.

FIG. 2 is a schematic diagram of pump 56, according to an embodiment of the present invention. Pump 56 is a piston pump, comprising a piston 64 which is driven by a motor 68 coupled to the piston. Cryogenic fluid pumps other than a piston pump such as pump 56, for example a bellows pump, may be used in embodiments of the present invention, and the description herein may be altered, mutatis mutandis to accommodate such different pumps.

Pump 56 is connected to a Dewar 72, which holds cryogenic fluid 52 that is retained in liquid form in a lower space 80 of the Dewar. Above the liquid in the Dewar, in an upper space 84, there is gas formed by evaporation of the cryogenic liquid.

As illustrated in FIG. 2, the piston of pump 56, and pump elements attached to the piston, are immersed in the liquid form of fluid 52. On operation of motor 68 the cryogenic fluid in liquid form exits from the Dewar via an outlet check valve 76 and an exit tube 94. The fluid exiting from valve 76 and tube 94 is typically approximately 100% liquid, and the exiting fluid from the pump is delivered to probe 60 via the exit tube.

Pump 56 is connected to receive returning cryogenic material from probe 60. The returning cryogenic material is typically a liquid-gas mixture, although in some cases the returning material may comprise approximately 100% gas, or possibly approximately 100% liquid. The returning material is input to a liquid/gas separator 88 via a receiving tube 92. Separator 88 returns separated cryogenic liquid to existing cryogenic liquid in space 52, and allows separated gas to enter into upper space 84.

Upper space 84 is connected via an exit tube 96 to a gas flow meter 100 (FIG. 4) which in turns connects to the atmosphere. Thus, separated gas entering upper space 84 is exhausted, via gas flow meter 100, to the atmosphere.

Figure 3:
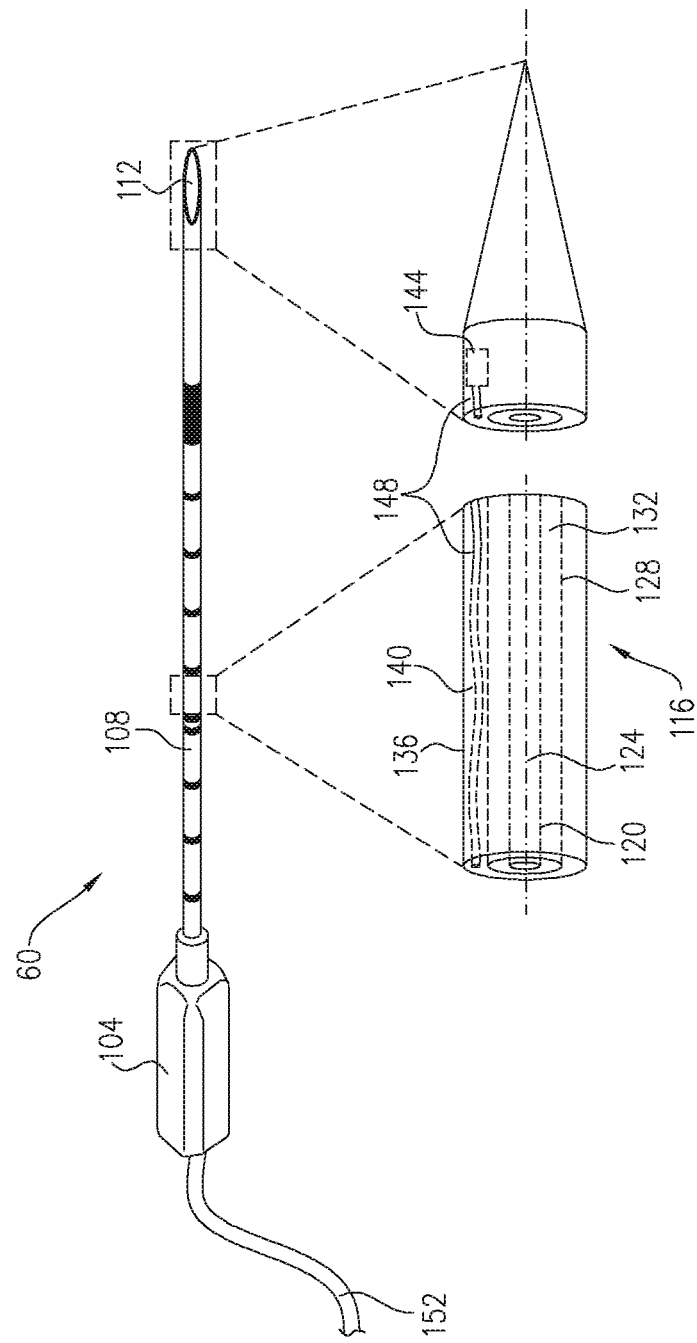
FIG. 3 is a schematic diagram of a probe, according to an embodiment of the present invention.

FIG. 3 is a schematic diagram of probe 60, according to an embodiment of the present invention. Probe 60 comprises a handle 104, which is attached to a shaft 108 of the probe at a shaft proximal end. Shaft 108 terminates in a pointed distal end 112, which enables the shaft to pierce tissue, such as a section of a breast of patient 28. As shown in a section 116, shaft 108 comprises three concentric tubes, typically formed from thin-walled stainless steel. A first, inner, tube 120 encloses a central lumen 124, and the inner tube is surrounded by a second tube 128. The first tube and the second tube are separated by an intermediate space 132. A third, outer, tube 136 surrounds second tube 128, and the second and third tubes are separated by a space 140.

A temperature sensor 144, typically a thermocouple or a thermistor, is fixedly located within distal end 112. Cabling 148 for the temperature sensor is typically positioned in space 140. The cabling is connected to processor 36, and enables the processor to measure a temperature sensed by sensor 144.

In operation of apparatus 20, space 140, between the second and third tubes of shaft 108, is maintained in a sealed evacuated state. As is explained in more detail below, central lumen 124 is used to convey cryogenic fluid from pump 56 to distal end 112, and intermediate space 132 is used to return cryogenic fluid from the distal end to the pump.

A flexible tube 152, having an internal structure generally similar to the internal structure of shaft 108, is coupled to the shaft via handle 104. Lumens within tube 152 are configured to convey cryogenic fluid from pump 56 to central lumen 124, and to transfer returning cryogenic fluid from intermediate space 132 to the pump.

Figure 4:
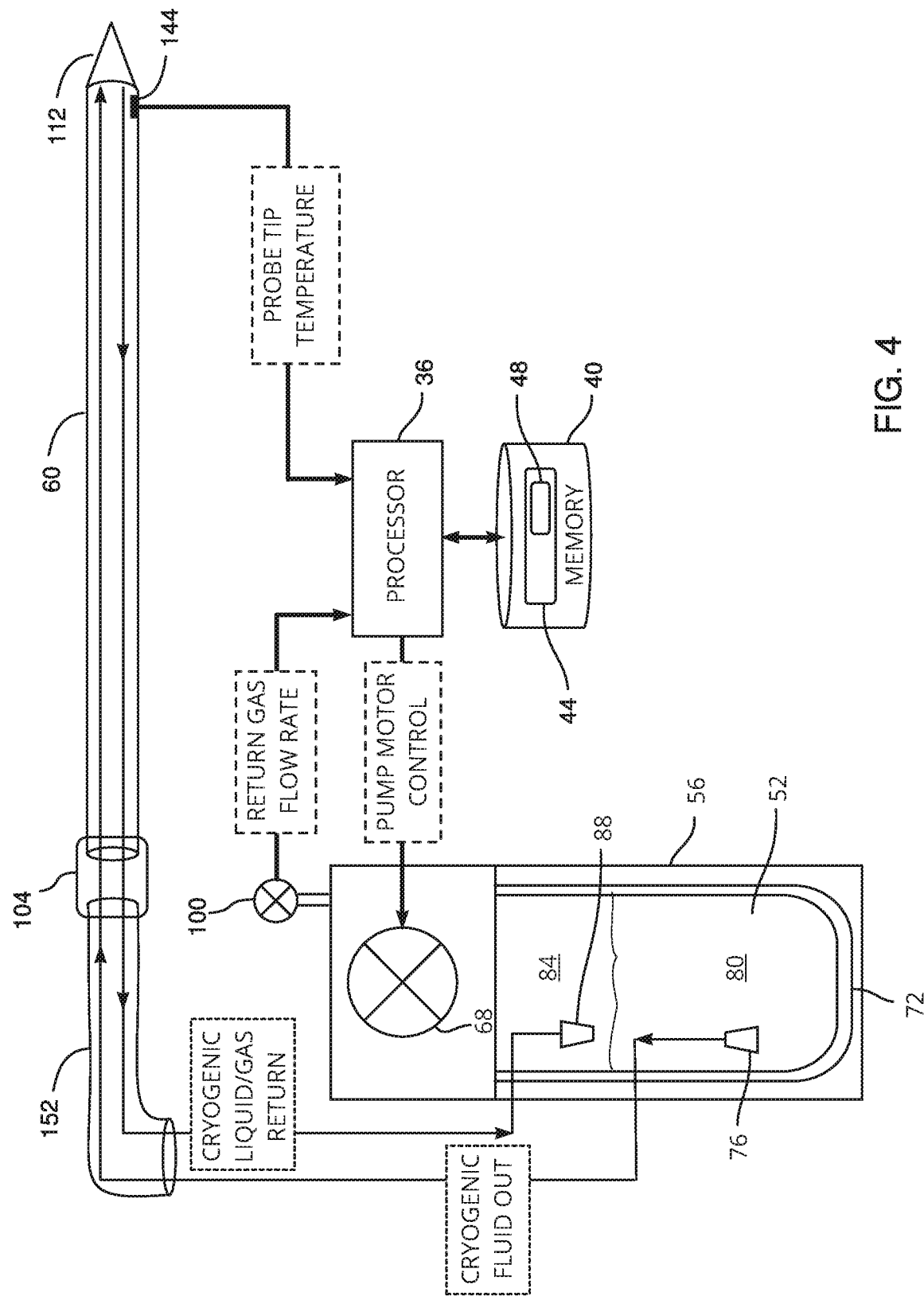
FIG. 4 is a schematic block diagram of the apparatus of FIG. 1, illustrating how the elements of the apparatus are connected together, according to an embodiment of the present invention.

FIG. 4 is a schematic block diagram of apparatus 20, illustrating how the elements of the apparatus are connected together, according to an embodiment of the present invention. The block diagram illustrates the flow of cryogenic fluid, and the flow of signal data, between the elements.

Processor 36 controls operation of apparatus 20, by providing pump motor control signals to motor 68. On activation, the motor operates pump 56 so that cryogenic fluid is expelled from Dewar 72 via output valve 76. The expelled cryogenic fluid flows out of the Dewar, via flexible tube 152 and handle 104, into probe 60 to distal end 112.

The cryogenic fluid returns from distal end 112, typically as a liquid/gas mixture, via probe 60, handle 104, and flexible tube 152 to liquid/gas separator 88 in Dewar 72. The separator divides the returning cryogenic fluid into gas, which enters upper space 84, and into liquid which enters lower space 80. The gas entering upper space 84 is exhausted to the atmosphere via gas flow meter 100.

As indicated in the figure, temperature sensor 144, at the distal end of the probe, provides a signal indicative of the temperature of the probe tip to processor 36. Processor 36 also receives, from gas meter 100, a signal indicative of the returning gas flow rate. This rate corresponds to the rate of flow of gas being input to space 84 from separator 88. Processor 36 uses these signals to operate algorithm 48, which enables the processor to generate an output signal controlling pump motor 68. The output signal that is transferred to the pump motor controls the revolution rate of the motor.

Figure 5A:
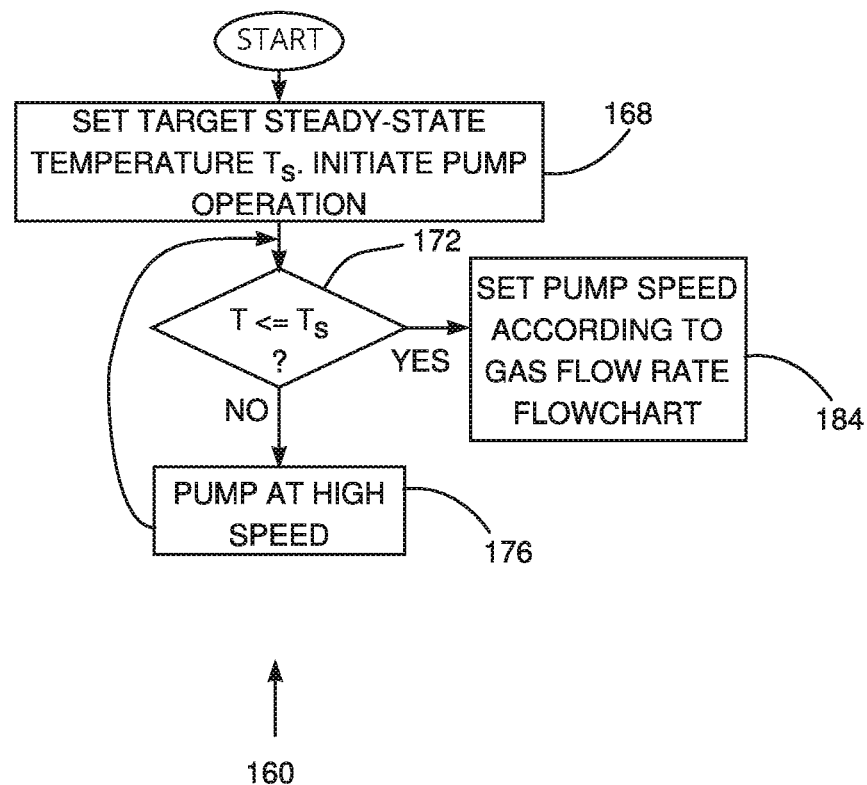
FIGS. 5A, 5B, 5C show flowcharts of steps followed by a processor in operating the apparatus, according to an embodiment of the present invention.
Figure 5B:
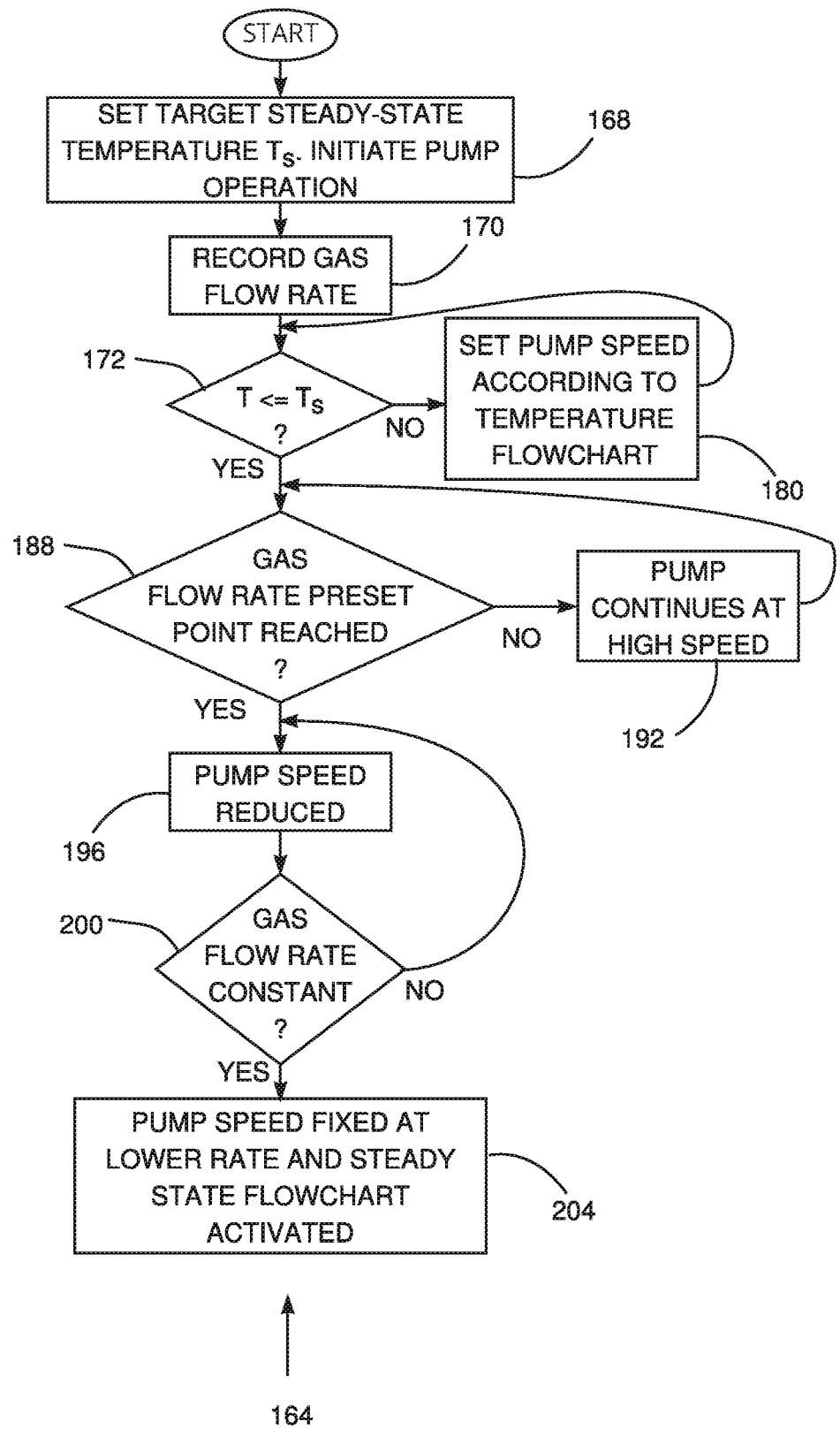
Figure 5C:
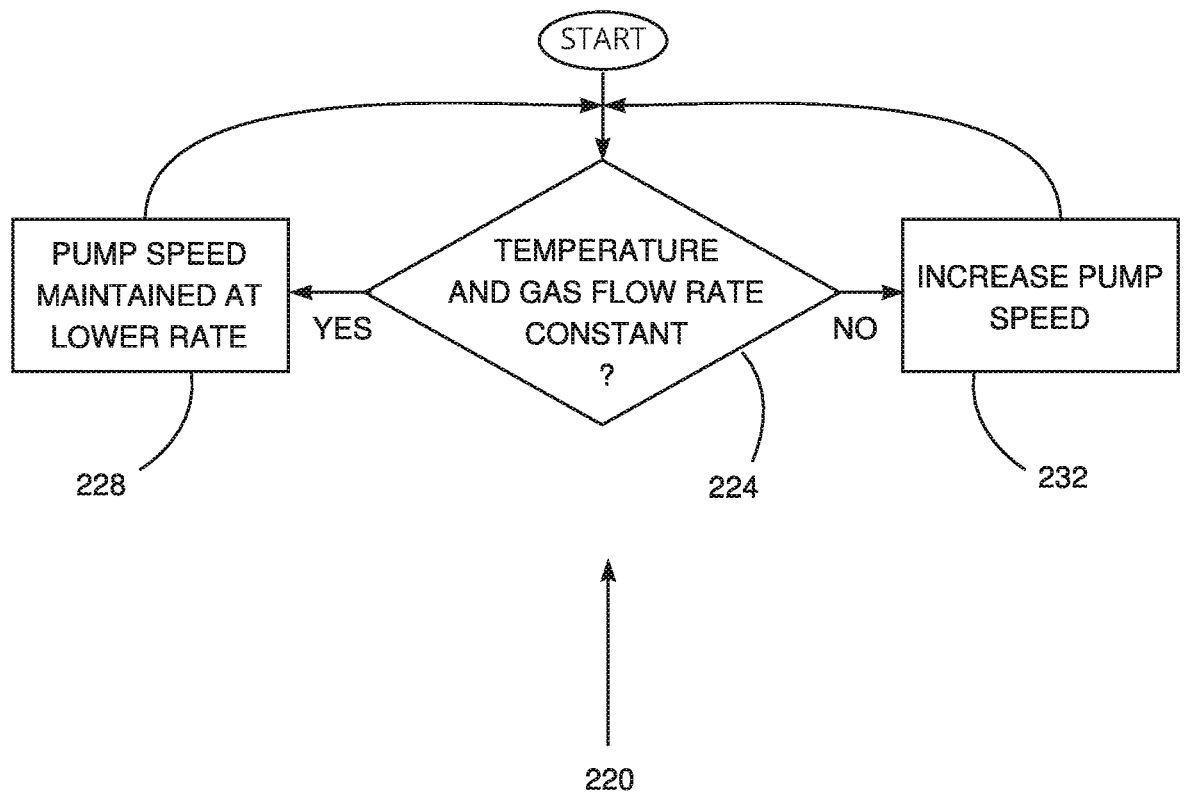
Figure 6:
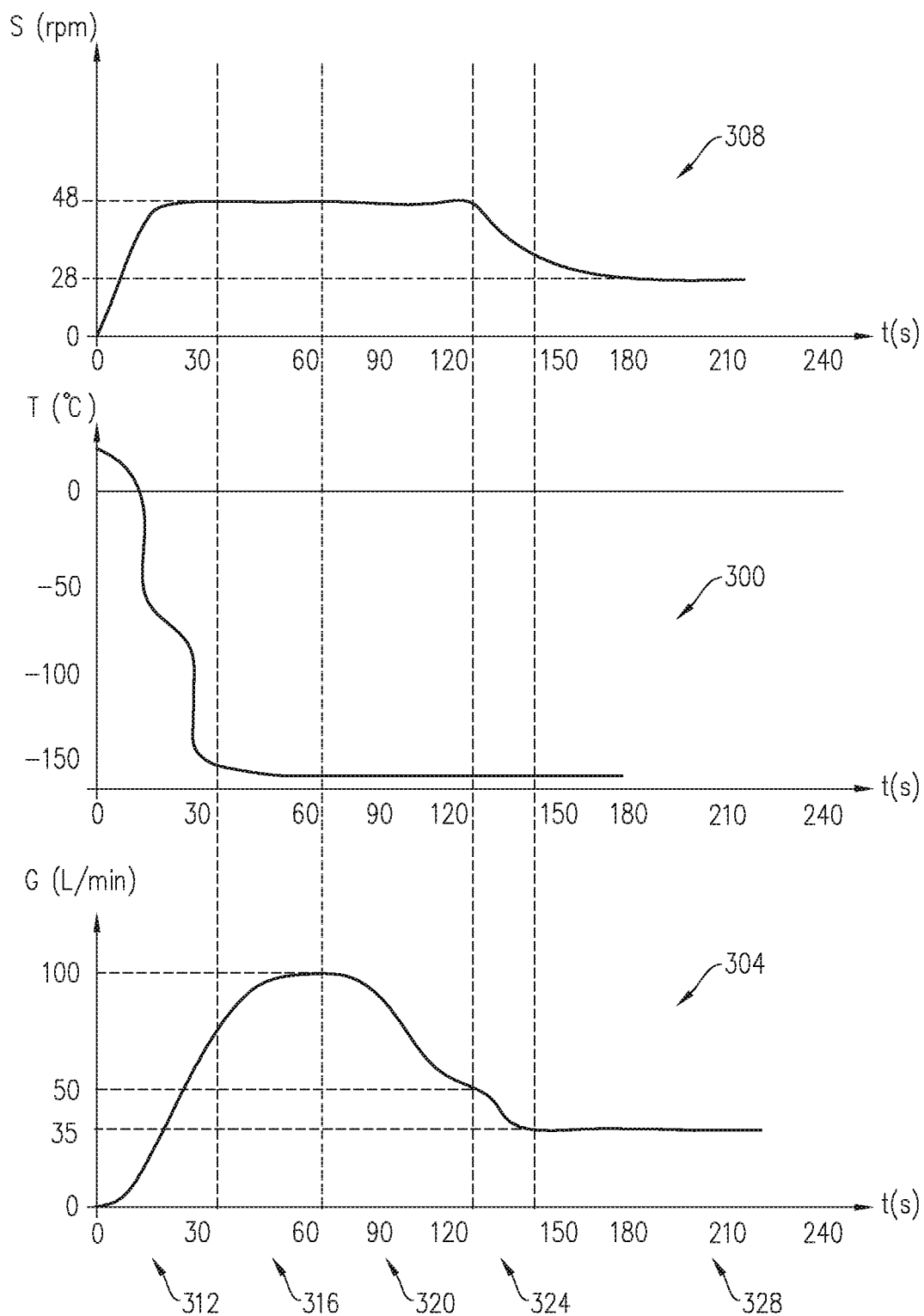
FIGS. 6 and 7 show graphs illustrating the steps of the flowcharts, according to an embodiment of the present invention.
Figure 7:
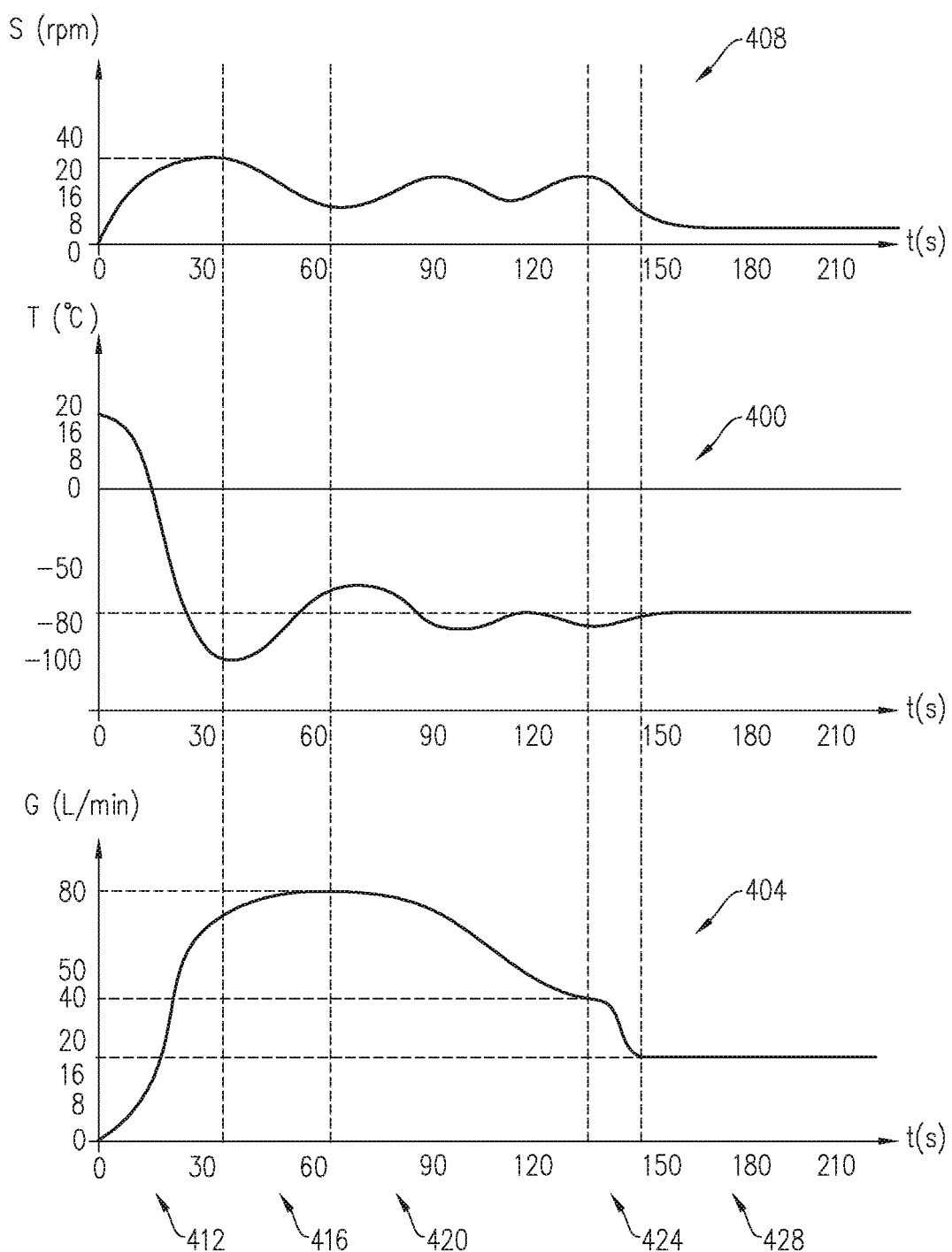

FIGS. 5A, 5B, 5C show flowcharts of steps followed by processor 36 in operating apparatus 20, and FIGS. 6 and 7 show graphs illustrating the steps of the flowcharts, according to an embodiment of the present invention. The steps of the flowcharts correspond to steps of algorithm 48.

Algorithm 48 comprises three flowcharts, a first flowchart 160, also herein termed temperature flowchart 160, a second flowchart 164, also herein termed gas flow rate flowchart 164, and a third flowchart 220, also herein termed steady state flowchart 220. In operating apparatus 20, the processor initially activates flowcharts 160 and 164 simultaneously, and steady state flowchart 220 is not activated. The processor activates flowcharts 160 and 164, typically after probe 60 has been positioned in a patient, with a command sent to processor 36 by physician 24 using console 42 to activate the flowcharts. (As explained below, steady state flowchart 220 is activated later.) On activation of flowcharts 160 and 164, in an initial operation step 168 in both flowcharts, physician 24 sets a target steady-state operating temperature $T_s$ for apparatus 20. The steady-state operating temperature $T_s$ of the apparatus is higher than the boiling point of cryogenic fluid 52, herein assumed to comprise liquid nitrogen (boiling point −196° C.) The steady-state operating temperature corresponds to the temperature of the probe tip that is maintained once the pump speed of motor 68 has been set, by processor 36, to a constant low speed. Typically, the steady-state operating temperature depends upon the constant low speed of the motor, so that the higher the constant low speed, the lower the steady-state operating temperature.

In a disclosed embodiment the constant low speed of motor 68 is approximately 28 rpm (revolutions per minute), for a steady-state operating temperature of approximately −160° C., and the constant low speed of the motor is approximately 8 rpm for a steady-state operating temperature of approximately −80° C. However, it will be understood that these values of constant low speed and steady-state operating temperature are by way of example, so that the scope of the present invention includes constant low speeds of motor 68 different from 8 rpm and 28 rpm, and corresponding steady-state temperatures different from −80° C. and −160° C. It will also be understood that the constant low speed required for a desired steady-state operating temperature may be determined without undue experimentation by one of ordinary skill in the art.

In addition, in initial step 168 processor 36 ramps the speed of motor 68 to a high speed.

In gas flow rate flowchart 164, control passes to a gas flow rate recordation step 170, wherein processor 36 records the gas flow rates of gas flow meter 100.

At initiation, probe 60 and its connecting flexible tube 152 are typically approximately at room temperature, and the processor accesses the signals from temperature sensor 144 in the probe tip to determine a probe tip temperature T. In a first decision step 172 in both flowcharts, the processor checks if temperature T is more than the steady-state operating temperature $T_s$ set in step 168.

In flowchart 160, if decision 1712 returns negative, i.e. if $T > T_s°$ C., then the flowchart proceeds to a high pump speed step 176, wherein the processor continues to operate motor 68 at a high speed. In a disclosed embodiment the high speed is in an approximate range of 40 rpm-50 rpm. Control in the flowchart then returns to decision 172, so that processor 36 reiterates the decision.

In flowchart 164, if decision 172 returns negative, then the flowchart proceeds to a transfer flowchart step 180, wherein the processor sets the speed of motor 68 according to temperature flowchart 160. From step 180 control returns to decision 172, so that, as for flowchart 160, processor 36 reiterates the decision.

The state when $T>T_s°$ C., occurring on initiation of the flowcharts, corresponds to an initial freeze process of apparatus 20.

FIG. 6 shows graphs for a procedure where steady-state temperature $T_s$ is approximately $-160°$ C., and FIG. 7 shows graphs for a procedure where steady-state temperature $T_s$ is approximately $-80°$ C. In FIG. 6 a graph 300 plots temperature T(° C.) vs. time(s), a graph 304 plots gas flow rate G(L/min) vs. time, and a graph 308 plots motor speed S(rpm) vs. time. In FIG. 7 a graph 400 plots temperature T(° C.) vs. time, a graph 404 plots gas flow rate G(L/min) vs. time, and a graph 408 plots motor speed S(rpm) vs. time.

As illustrated in the graphs, in first initiation periods 312 and 412, typically of duration of approximately 30 s from initiation of operation of apparatus 20, temperature T reduces sharply to approximately $-160°$ C. (FIG. 6) and $-80°$ C. (FIG. 7), while the speed rate S of motor 68 ramps up to a high rate of 48 rpm (FIG. 6) and 30 rpm (FIG. 7). This period corresponds to the time during which decision 172 reiterates.

In flowchart 160, when decision 172 returns positive, i.e., $T \leq T_s$, control moves to a gas flow rate flowchart step 184, where the processor sets the speed of motor 68 according to flowchart 164. Even though the processor accesses flowchart 164, the processor continues to iterate decision 172, to check that the inequality $T \leq T_s$ continues to return positive.

In flowchart 164, when decision 172 returns positive, control moves to a second decision 188, where the processor accesses the signal indicative of the flow rate of gas flow meter 100. In second decision 188, the processor checks if the flow rate of gas through meter 100 has fallen from a high value to a predetermined lower gas flow rate. The predetermined lower gas flow rate is a gas flow rate which, when achieved, indicates that the speed of motor 68 may be reduced without adversely affecting a steady-state temperature that has been reached. The predetermined lower gas flow rate may be found by one of ordinary skill in the art, without undue experimentation.

As illustrated by the graphs, in first initiation periods 312, 412 the gas flow rate typically initially increases from zero. Even when the first initiation period has finished, the graphs illustrate that the gas flow rate continues to increase, typically to a peak high value of approximately 100 L/min in a second initiation period 316 (FIG. 6) and to a peak high value of approximately 80 L/min in a second initiation period 416 (FIG. 7). In an embodiment second initiation periods 316, 416 have a duration of approximately 30 s, after the end of the first initiation period. In a third initiation period 320 (FIG. 6) and a third initiation period 420 (FIG. 7), beginning at the termination of the second initiation period, the gas flow rate then begins to decrease, while still remaining relatively high until it reaches the predetermined lower gas flow rate.

The predetermined lower gas flow rate is less than 100% of the peak high value rate, and is typically set as a fraction, i.e., a percentage, of the peak high value rate. In one embodiment the percentage is set at approximately 50%, so that for a peak high value of approximately 100 L/min the predetermined lower gas flow rate is approximately 50 L/min (FIG. 6) and for a peak high value of approximately 80 L/min the predetermined lower gas flow rate is approximately 40 L/min (FIG. 7). It will be understood that the value of 50% is approximate and exemplary, so that the scope of the present invention comprises values for the predetermined lower gas flow rate being lower or higher than 50% of the peak high value rate.

The high gas flow rates during the first three initiation periods are due to the cryogenic fluid cooling elements of apparatus 20, including flexible tube 152 and probe 60. As the elements approach an approximate steady state, the gas flow rate approaches an approximately steady-state value.

As stated above, in second decision step 188 processor 36 checks if the flow rate of gas through meter 100 has fallen from a high value to a predetermined lower value gas flow rate. The processor performs this check by accessing the gas flow rates stored in step 170.

If second decision step 188 returns negative, i.e., the gas flow rate has not reached the predetermined lower value gas flow rate, control passes to a high speed pump step 192, wherein the processor continues to maintain the speed S of motor 68 at a high rate. From step 192 control returns to the second decision step, so that the processor reiterates this step.

If second decision step 188 returns positive, i.e., the gas flow rate has reached the predetermined lower value gas flow rate, control passes to a reduce pump speed step 196, wherein the processor iteratively reduces the speed of motor 68 by a preset fraction or percentage, herein assumed to be 10%, although the preset percentage may be lower or higher than this value. As explained below, the iteration of step 196 is contingent on a third decision 200 returning negative.

Second decision step 188 returning positive corresponds to third initiation period 320 (FIG. 6) and third initiation period 420 (FIG. 7) terminating, and transition periods 324 and 424 starting.

From step 196 control passes to third decision step 200, wherein processor 36 checks if the gas flow rate has reduced to an approximately constant value. In one embodiment the approximately constant value is approximately 35 L/min when $T_s=-160°$ C., and approximately 18 L/min when $T_s=-80°$ C., but other embodiments may have approximate constant values that for the values of $T_s$ are higher or lower than these values.

If the third decision returns negative, so that the gas flow rate is not approximately constant, then control returns to reduce pump speed step 196, so that a further reduction in motor speed is performed, and the third decision reiterates.

If the third decision returns positive, so that the gas flow rate is approximately constant, then control transfers to a set pump speed at lower rate step 204, wherein the processor reduces the speed of motor 68 gradually to a preset fixed lower rate. In one embodiment the fixed lower rate is approximately 28 rpm for $T_s=-160°$ C., and approximately 8 rpm when $T_s=-80°$ C.

Third decision 200 returning positive corresponds to apparatus 20 achieving a steady state, so that step 204 also includes activation of steady state flowchart 220. The achievement of steady state corresponds to the termination of transition period 324, and the beginning of a steady state period 328 (FIG. 6), and to the termination of transition period 424, and the beginning of a steady state period 428 (FIG. 7).

At the beginning of steady state periods 328 and 428, i.e., on implementation of step 204, the processor ceases operation of temperature flowchart 160 and gas flow rate flowchart 164, and activates steady state flowchart 220.

In steady state flowchart 220, in a decision step 224 the processor checks if the temperature T and flow rate G are both constant. If the decision returns positive, then in a maintain pump speed constant step 228 the processor keeps motor 68 at its low speed. If the decision returns negative, then in an increase pump speed step 232 the processor increases the speed of motor 68 by a preset amount, typically approximately 2-6 rpm. After both steps 228 and 232 control returns to decision step 224, which processor 36 reiterates.

It will be appreciated that by measuring both the temperature of the distal end of the probe, and the rate of flow of returning cryogenic gas, embodiments of the invention considerably improve the efficiency of operation of a cryogenic pumping system. Using both the temperature and the rate of flow enables a steady state low temperature to be achieved and maintained, while reducing the volume of cryogenic fluid used compared to prior art systems.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus for cryogenic treatment of a tissue of a living subject, the apparatus comprising:
   a probe, containing a lumen and having a distal end configured to contact the tissue of the living subject;
   a temperature sensor located at the distal end;
   a pump, comprising a pump motor, coupled to deliver a cryogenic fluid through the lumen to the distal end of the probe and to receive the cryogenic fluid returning from the probe;
   a separator, coupled to separate the returning cryogenic fluid into a returning cryogenic liquid and a returning cryogenic gas;
   a flow meter, coupled to measure a rate of flow of the returning cryogenic gas; and
   a processor configured to control a rate of pumping of the pump motor in response to a temperature measured by the temperature sensor and the rate of flow of the returning cryogenic gas.

2. The apparatus according to claim 1 wherein the pump comprises a piston pump.

3. The apparatus according to claim 1 wherein the pump comprises a bellows pump.

4. The apparatus according to claim 1 wherein, while the temperature reduces, the processor sets the rate of pumping to a preset high rate.

5. The apparatus according to claim 1 wherein, when the temperature has reduced to a predetermined steady-state value, the processor sets the rate of pumping to a preset high rate until the rate of flow of the returning cryogenic gas reduces from a measured peak high value rate of flow to a predetermined lower rate of flow.

6. The apparatus according to claim 5 wherein, when the rate of flow of the returning cryogenic gas comprises the predetermined lower rate of flow, the processor reduces the rate of pumping to a preset rate lower than the preset high rate.

7. The apparatus according to claim 6, wherein, when the rate of pumping has been reduced to the lower preset rate, the processor increases the rate of pumping when at least one of the temperature and the rate of flow changes.

8. The apparatus according to claim 5, wherein the predetermined lower rate of flow is a preset percentage, less than 100%, of the measured peak high value rate of flow.

9. The apparatus according to claim 8, wherein the preset percentage is 50%.

10. The apparatus according to claim 1, wherein when the temperature comprises a first steady-state temperature measured by the temperature sensor the processor sets the rate of pumping at a first rate, and when the temperature comprises a second steady-state temperature less than the first steady-state temperature the processor sets the rate of pumping at a second rate greater than the first rate.

11. A method of operating a cryogenic pumping system, comprising:
    providing a probe containing a lumen and having a distal end, that is configured to contact tissue of a living subject;
    locating a temperature sensor at the distal end;
    coupling a pump, comprising a pump motor, to deliver a cryogenic fluid through the lumen to the distal end of the probe and to receive the cryogenic fluid returning from the probe;
    separating the returning cryogenic fluid into a returning cryogenic liquid and a returning cryogenic gas;
    measuring a rate of flow of the returning cryogenic gas; and
    controlling a rate of pumping of the pump motor in response to a temperature measured by the temperature sensor and the rate of flow of the returning cryogenic gas.

12. The method according to claim 11 wherein the pump comprises a piston pump.

13. The method according to claim 11 wherein the pump comprises a bellows pump.

14. The method according to claim 11 further comprising, while the temperature reduces, setting the rate of pumping to a preset high rate.

15. The method according to claim 11 further comprising, when the temperature has reduced to a predetermined steady-state value, setting the rate of pumping to a preset high rate until the rate of flow of the returning cryogenic gas reduces from a measured peak high value rate of flow to a predetermined lower rate of flow.

16. The method according to claim 15 further comprising, when the rate of flow of the returning cryogenic gas comprises the predetermined lower rate of flow, reducing the rate of pumping to a preset rate lower than the preset high rate.

17. The method according to claim 16, further comprising, when the rate of pumping has been reduced to the lower preset rate, increasing the rate of pumping when at least one of the temperature and the rate of flow changes.

18. The method according to claim 15, wherein the predetermined lower rate of flow is a preset percentage, less than 100%, of the measured peak high value rate of flow.

19. The method according to claim 18, wherein the preset percentage is 50%.

20. The method according to claim 11, wherein when the temperature comprises a first steady-state temperature measured by the temperature sensor the rate of pumping is set at a first rate, and when the temperature comprises a second steady-state temperature less than the first steady-state temperature the rate of pumping is set at a second rate greater than the first rate.

\* \* \* \* \*